(12) United States Patent
Chisholm (10) Patent No.: US 8,512,270 B2
(45) Date of Patent: *Aug. 20, 2013

(54) DYNAMIC FOOT-ARCH SUPPORT ASSEMBLY AND ASSOCIATED METHODS

(76) Inventor: Donna Chisholm, Dalzell, SC (US)

(*) Notice: Subject to any disclaimer, the term of this patent is extended or adjusted under 35 U.S.C. 154(b) by 211 days.

This patent is subject to a terminal disclaimer.

(21) Appl. No.: 13/175,871

(22) Filed: Jul. 3, 2011

(65) Prior Publication Data

US 2011/0258880 A1 Oct. 27, 2011

Related U.S. Application Data

(63) Continuation-in-part of application No. 12/029,503, filed on Feb. 12, 2008, now Pat. No. 7,972,290.

(51) Int. Cl.
*A61F 13/00* (2006.01)
(52) U.S. Cl.
USPC .................................. 602/66; 602/60; 602/62

(58) Field of Classification Search
USPC ............ 602/65–66, 30; 36/8.3, 132; 66/178, 66/185
See application file for complete search history.

(56) References Cited

U.S. PATENT DOCUMENTS

| 1,441,907 A | 1/1923 | Bernstein |
| 5,928,173 A | 7/1999 | Unruh |

*Primary Examiner* — Kim M Lewis (57) ABSTRACT

The technology described herein provides a dynamic foot-arch support assembly for dynamically supporting the arch and structures of the human foot throughout phases of the biomechanical movement of the foot during weight-bearing activities. A dynamic foot-arch support assembly for supporting the arch and structures of a foot is provided that includes a support band having an upper end and a lower end, the support band forming a loop at the upper end through which to place a foot and position the loop around or just below an ankle portion of the foot, the lower end configured to wrap from an inside area of the ankle portion of the foot and rotate to an underside of the foot for secure attachment below the underside of the foot, the support band thereby configured to provide a tension to support an arch area of the foot, and a shoe sole, the lower end configured secured to the shoe sole.

9 Claims, 8 Drawing Sheets

DYNAMIC FOOT-ARCH SUPPORT ASSEMBLY AND ASSOCIATED METHODS

CROSS-REFERENCE TO RELATED APPLICATION(S)

This present non-provisional patent application is a continuation-in-part of copending U.S. patent application Ser. No. 12/029,503 filed on Feb. 12, 2008, and entitled "Dynamic Foot-arch Support System and Associated Methods," and of which the application cited above is incorporated in-full by reference herein.

FIELD OF THE INVENTION

The technology described herein relates generally to support devices and assemblies for protecting anatomical parts. More specifically, the technology described herein relates to a dynamic foot-arch support assembly, and associated methods, for dynamically supporting the arch and structures of the human foot throughout phases of the biomechanical movement of the foot during weight-bearing activities.

BACKGROUND OF THE INVENTION

The human feet endure a multiplicity of strong forces in order to support and balance the weight of the entire body during ordinary daily activities. In fact, the feet are the primary weight-bearing elements of the upright body. By way of example, supporting the arch and structures in the feet aids a person who is standing, walking, running, etc. Additionally, such support can decrease undesired stresses upon the arch and structures of the feet.

These and other problems exist. Previous attempts to solve these and other problems include the following: U.S. Pat. No. 1,441,907, issued to Bernstein on Jan. 9, 1923, which discloses an arch and ankle support; U.S. Pat. No. 5,928,173, issued to Unruh on Jul. 27, 1999, which discloses a turf toe brace.

The foregoing patent and other information reflect the state of the art of which the inventor is aware and are tendered with a view toward discharging the inventor's acknowledged duty of candor in disclosing information that may be pertinent to the patentability of the technology described herein. It is respectfully stipulated, however, that the foregoing patent and other information do not teach or render obvious, singly or when considered in combination, the inventor's claimed invention.

BRIEF SUMMARY OF THE INVENTION

In various exemplary embodiments, the technology described herein provides a dynamic foot-arch support device for dynamically supporting the arch and structures of the human foot throughout phases of the biomechanical movement of the foot during weight-bearing activities.

In one exemplary embodiment, the technology described herein provides a dynamic foot-arch support device for dynamically supporting the arch and structures of a foot throughout phases of the biomechanical movement of the foot during weight-bearing activities, the device comprising a support band having a generally rectangular shape having a length and a width, comprised of an elongated, flexible material that is elastic in length and inelastic in width, an upper end and a lower end, the support band forming a fixed loop at the upper end through which to place a foot and position the fixed loop around an area about or just below an ankle portion of the foot, the lower end configured to wrap from an inside of the area about or just below the ankle portion of the foot and rotate 180 degrees to an underside of the foot and across a plantar surface area for secure attachment below the underside of the foot, the support band thereby configured to provide an adjustable tension to support to an arch area of the foot; and a footwear, e.g. a shoe, having a sole, at least one portion of the support band integrally formed with the sole at a predetermined angle.

In another exemplary embodiment, the technology described herein provides a dynamic foot-arch support assembly for dynamically supporting the arch and structures of a foot throughout phases of the biomechanical movement of the foot during weight-bearing activities, the device comprising a support band having a generally rectangular shape having a length and a width, comprised of an elongated, flexible material that is elastic in length and inelastic in width, an upper end and a lower end, the support band forming a fixed loop at the upper end through which to place a foot and position the fixed loop around an area about or just below an ankle portion of the foot, the lower end configured to wrap from an inside of the area about or just below the ankle portion of the foot and rotate 180 degrees to an underside of the foot and across a plantar surface area for secure attachment below the underside of the foot, the support band thereby configured to provide an adjustable tension to support to an arch area of the foot; and a shoe having a sole, the lower end of the support band secured to the sole at a predetermined angle.

In still another exemplary embodiment the technology described herein provides a dynamic foot-arch support assembly for dynamically supporting the arch and structures of a foot throughout phases of the biomechanical movement of the foot during weight-bearing activities, the device comprising a support band having a generally rectangular shape having a length and a width, comprised of an elongated, flexible material that is elastic in length and inelastic in width, an upper end and a lower end, the support band forming a fixed loop at the upper end through which to place a foot and position the fixed loop around an area about or just below an ankle portion of the foot, the lower end configured to wrap from an inside of the area about or just below the ankle portion of the foot and rotate 180 degrees to an underside of the foot and across a plantar surface area for secure attachment below the underside of the foot, the support band thereby configured to provide an adjustable tension to support to an arch area of the foot; and a shoe having a sole, the lower end of the support band releaseably attached to the sole at a predetermined angle.

In yet another exemplary embodiment, the technology described herein provides a dynamic foot-arch support device for supporting the arch and structures of a foot. The dynamic foot-arch support device includes a support band having an upper end and a lower end, the support band forming a loop at the upper end through which to place a foot and position the loop around an area about or just below an ankle portion of the foot, the lower end configured to wrap from an inside of the area about or just below the ankle portion of the foot and rotate to an underside of the foot and across a plantar surface area for secure attachment below the underside of the foot, the support band thereby configured to provide a tension to support to an arch area of the foot. The support band is configured to provide a supportive, counter-reactive force to the arch and structures of the foot during biomechanical movement of the foot during weight-bearing activities. The arch area of the foot is sustained as the foot alternates between weight-bearing and non-weight-bearing activities.

In one embodiment, the support band of the dynamic foot-arch support device is an elongated, flexible elastic strap. A length of the support band is adjustable to accommodate varying foot sizes.

The dynamic foot-arch support device also includes a forefoot cover securely attached to the lower end of the support band and configured for placement over a toe area of the foot, wherein the tension is formed on the support band between the forefoot cover and the loop placed around an area about or just below an ankle portion of the foot providing support to the plantar surface. In one embodiment, the lower end of the support band is securely attached to the forefoot cover at a predetermined angle to maximize support to a plantar portion of the foot.

Alternatively, the lower end of the support band is configured for secure attachment to a sole of footwear, e.g., a shoe, boot, slipper, sandal. The tension is formed on the support band between the sole and the loop around an area about or just below an ankle portion of the foot providing support to the plantar surface.

Alternatively, the support band is integrally formed with a shoe via the top, foot-facing portion of a shoe sole, i.e. the inner sole.

Alternatively, the support band is integrally formed with a sock.

In another exemplary embodiment, the technology described herein provides a method for supporting the arch and structures of a foot. The method includes utilizing a support band having an upper end and a lower end, forming a loop at the upper end of the support band through which to place a foot and position the loop around an area about or just below an ankle portion of the foot, configuring the lower end to wrap from an inside of the area about or just below the ankle portion of the foot and rotate to an underside of the foot and across a plantar surface area for secure attachment below the underside of the foot, and configuring the support band to provide a tension to support to an arch area of the foot. The method also includes providing biomechanical arch and foot support with a supportive, counter-reactive force to the arch and structures of the foot during biomechanical movement of the foot during weight-bearing activities. The method also includes providing support to the arch area of the foot as the foot alternates between weight-bearing and non-weight-bearing activities. The support band is an elongated, flexible elastic strap. A length of the support band is configured to be adjustable to accommodate varying foot sizes.

The method also includes utilizing a forefoot cover, attaching the forefoot cover securely to the lower end of the support band, and configuring the forefoot cover for placement over a toe area of the foot. The tension is formed on the support band between the forefoot cover and the loop placed around an area about or just below an ankle portion of the foot providing support to the plantar surface. The method also includes attaching the lower end of the support band to the forefoot cover at a predetermined angle to maximize support to a plantar portion of the foot.

Alternatively, the method also includes configuring the lower end of the support band for secure attachment to a sole of footwear, e.g. a shoe, a boot, a slipper, a sandal. In one embodiment of this method the secure attachment to the sole is via the top portion of the shoe sole. The tension is formed on the support band between the sole and the loop around an area about or just below an ankle portion of the foot providing support to the plantar surface. Alternatively, the support band is integrally formed with a sock.

There has thus been outlined, rather broadly, the more important features of the technology in order that the detailed description thereof that follows may be better understood, and in order that the present contribution to the art may be better appreciated. There are additional features of the technology that will be described hereinafter and which will form the subject matter of the claims appended hereto. In this respect, before explaining at least one embodiment of the technology in detail, it is to be understood that the invention is not limited in its application to the details of construction and to the arrangements of the components set forth in the following description or illustrated in the drawings. The technology described herein is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the technology described herein.

Further objects and advantages of the technology described herein will be apparent from the following detailed description of a presently preferred embodiment which is illustrated schematically in the accompanying drawings.

BRIEF DESCRIPTION OF THE DRAWINGS

The technology described herein is illustrated with reference to the various drawings, in which like reference numbers denote like device components and/or method steps, respectively, and in which.

DETAILED DESCRIPTION OF THE INVENTION

Before describing the disclosed embodiments of this technology in detail, it is to be understood that the technology is not limited in its application to the details of the particular arrangement shown here since the technology described is capable of other embodiments. Also, the terminology used herein is for the purpose of description and not of limitation.

In various exemplary embodiments, the technology described herein provides a dynamic foot-arch support device for dynamically supporting the arch and structures of the human foot throughout phases of the biomechanical movement of the foot during weight-bearing activities.

Figure 1:
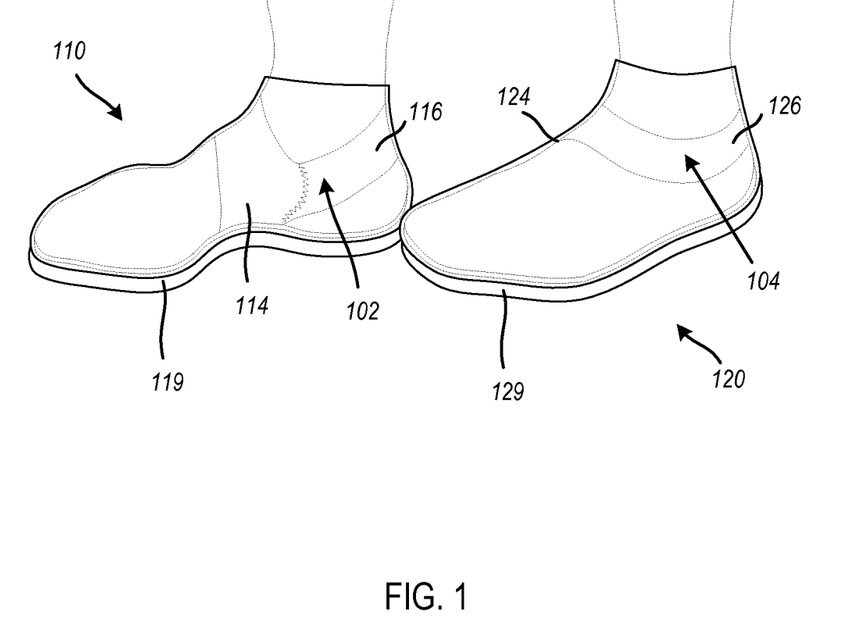
FIG. 1 is an elevational view of a dynamic foot-arch support assembly, illustrating the assembly integrated into footwear being worn by a user, according to an embodiment of the technology.
Figure 2:
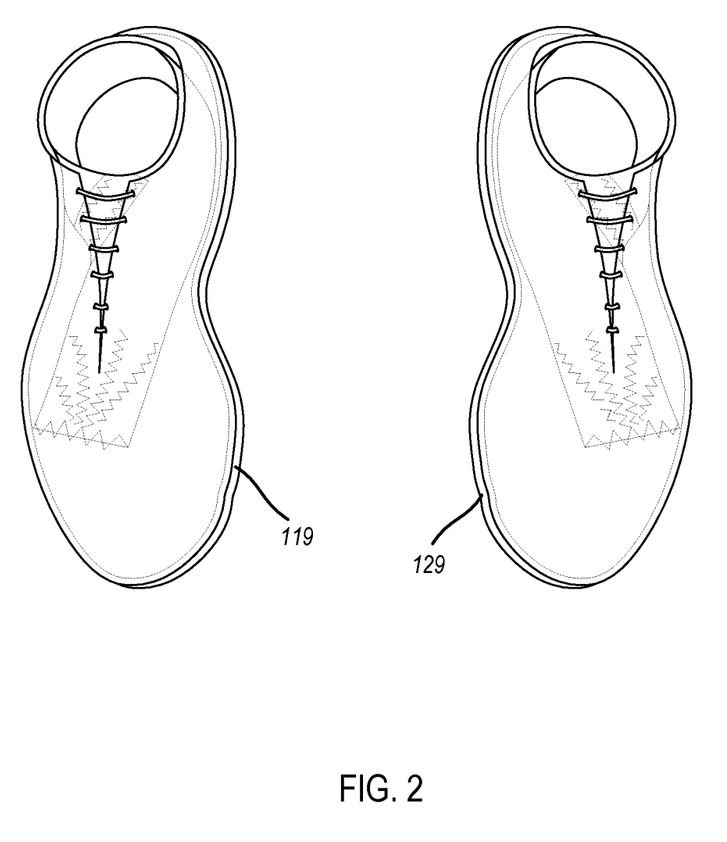
FIG. 2 is a top elevational view of the dynamic foot-arch support assembly depicted in FIG. 1, illustrating, in particular, stitching securing the support band to the sole of footwear.
Figure 3:
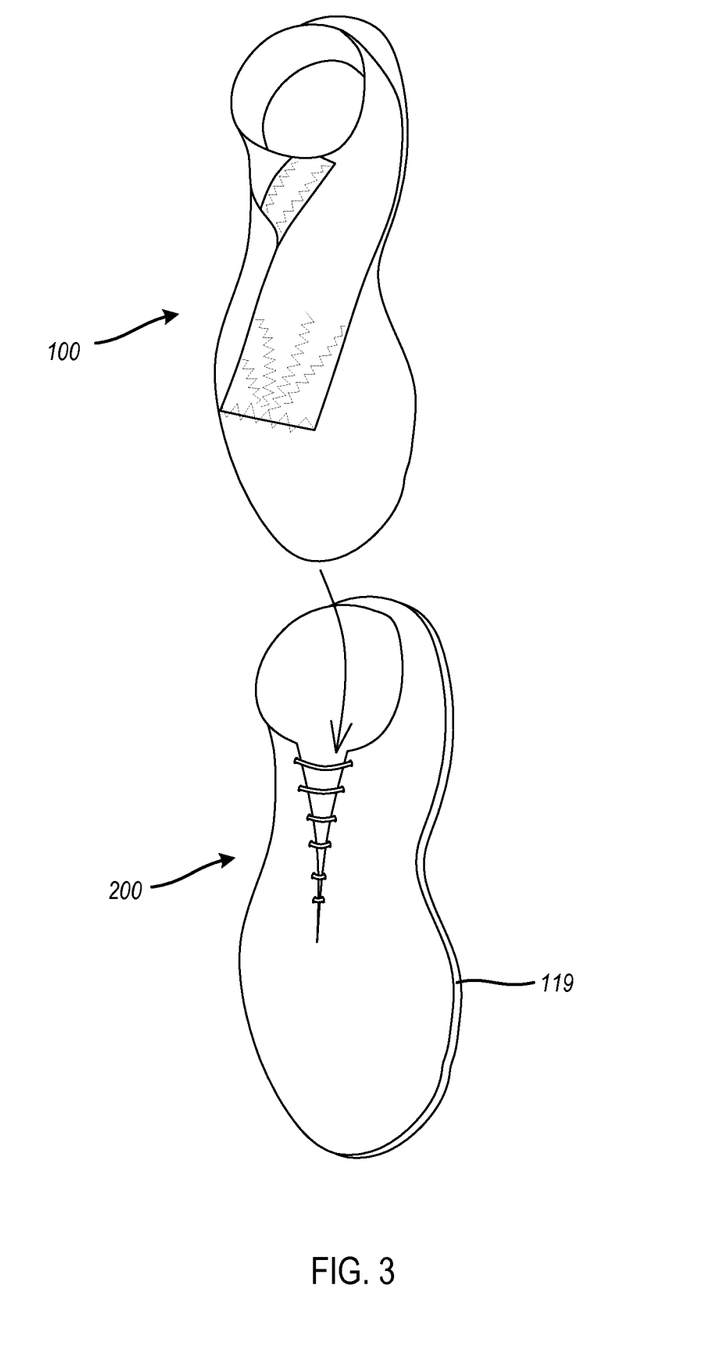
FIG. 3 is a partially exploded view of a dynamic foot-arch support assembly, illustrating, in particular the integrated support band and their relationship to the corresponding footwear, according to an embodiment of the technology.
Figure 4:
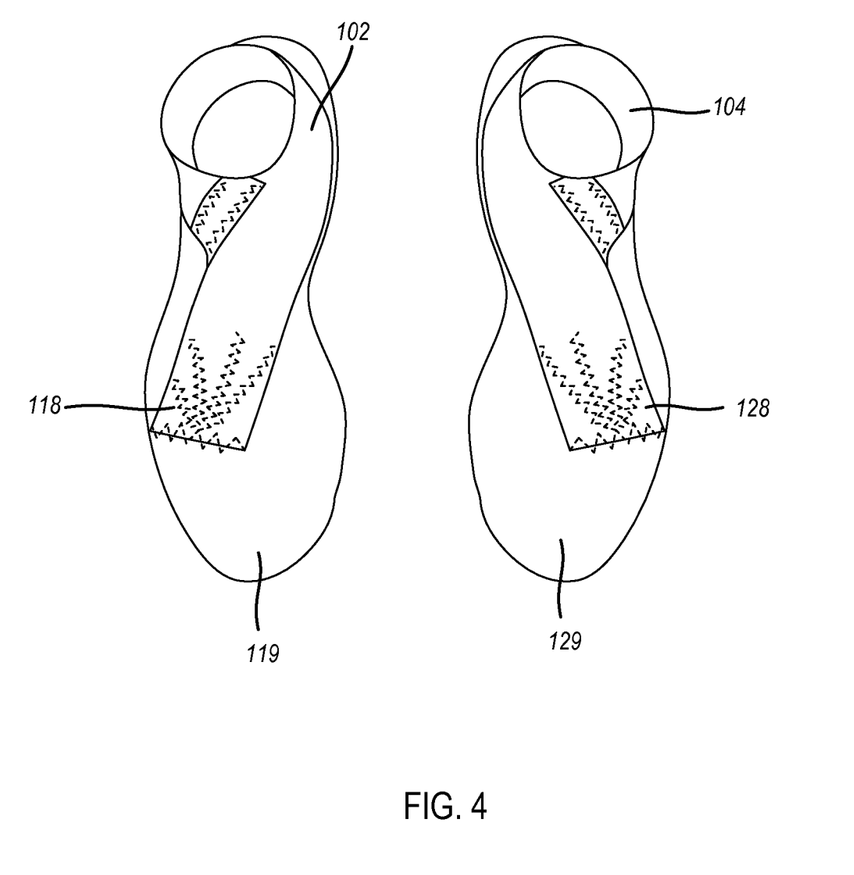
FIG. 4 is a top elevational view of a dynamic foot-arch support assembly, illustrating, in particular, a pair of shoe soles with support bands secured, according to an embodiment of the technology.
Figure 5:
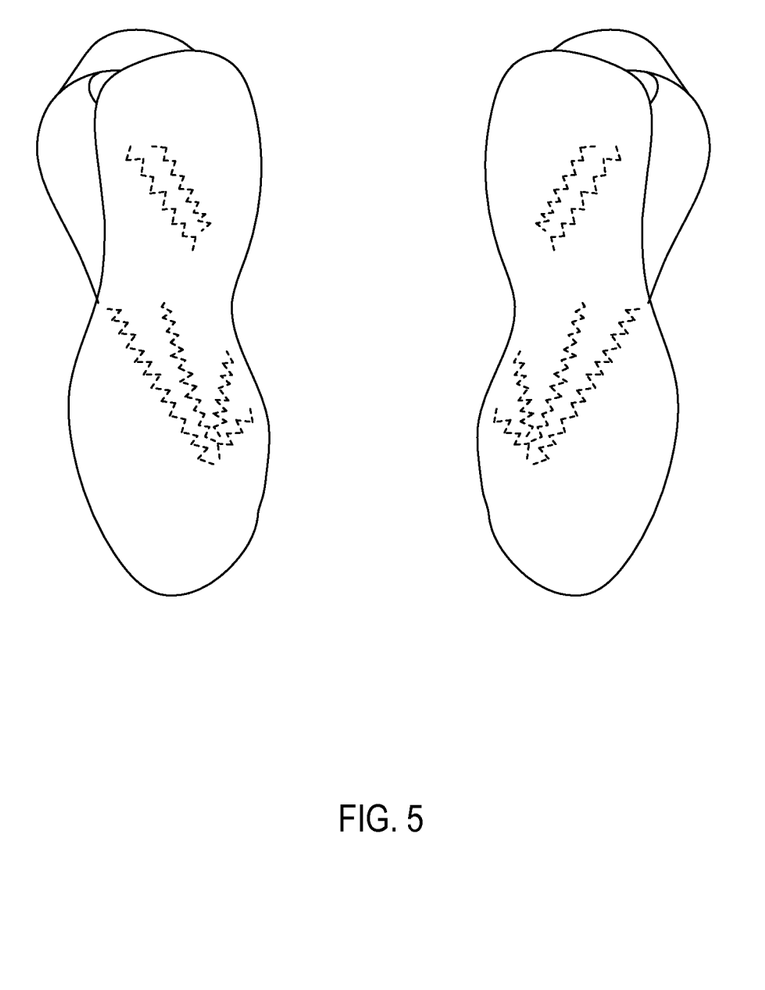
FIG. 5 is a bottom elevational view of a dynamic foot-arch support device, illustrating, in particular, the stitching securing the support band to the shoe sole.
Figure 6:
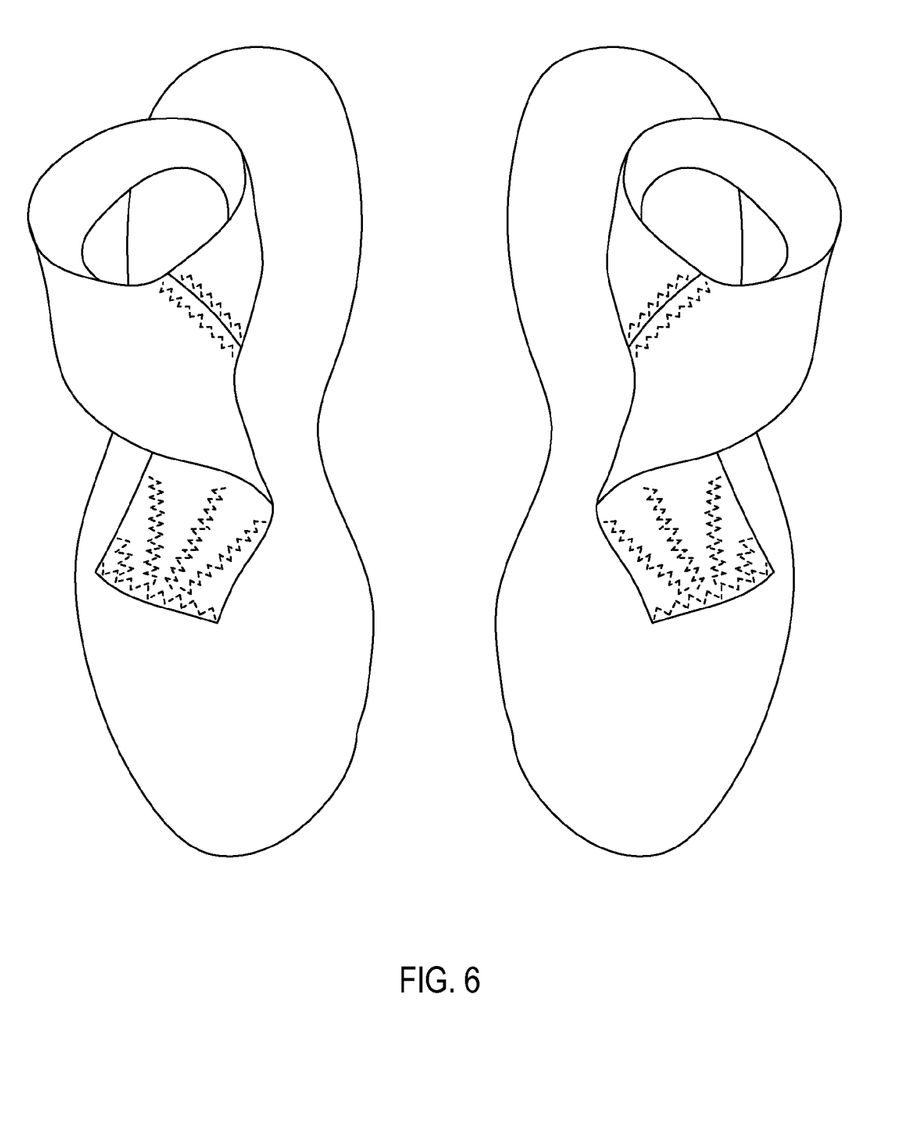
FIG. 6 is a top elevational view of a dynamic foot-arch support assembly, illustrating, in particular, a pair of shoe soles with support bands secured, according to an embodiment of the technology.

Referring now to FIGS. 1-8, a dynamic foot-arch support assembly 100 for supporting the arch and structures of a foot is shown. As depicted in FIG. 1, a dynamic foot-arch support device 100 is provided. The dynamic foot-arch support device 100 is suitable for, and is shown on, both a right foot 110 and a left foot 120. The dynamic foot-arch support device 100 is a supportive piece of footwear designed for general use by wearers performing weight-bearing activities such as, for example and not limited to, dynamic standing, walking, jogging, or running. The dynamic foot-arch support device 100 provides intimate support contact to the foot thereby providing support to the arch and other structures of the foot through the biomechanical phases of foot movement.

The dynamic foot-arch support device 100 provides biomechanical arch and foot support with a supportive, counter-reactive force to the arch and structures of the foot during biomechanical movement of the foot during weight-bearing activities. The dynamic foot-arch support device 100 also provides support to the arch area of the foot as the foot alternates between weight-bearing and non-weight-bearing activities.

Figure 8:
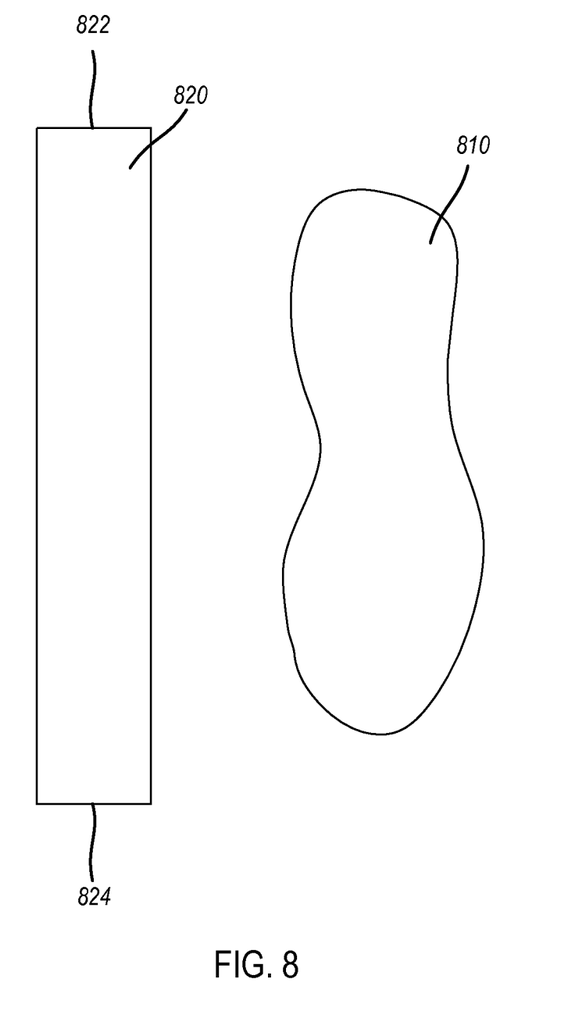
FIG. 8 is a top plan view of the band and shoe sole depicted in FIG. 7.

The dynamic foot-arch support device 100 includes a support band 102 (on the right foot), 104 (on the left foot) generally of the original shape 820 as shown in FIG. 8. The biomechanical support to the arch and structures of the foot is provided by the functional design of the support band 102, 104 and by the flexible material with which the support band 102, 104 is fabricated. The support band 102, 104 is generally rectangular in shape and includes two ends, and upper end 822, and a lower end 824, as depicted in FIG. 8. Length of the support band 102, 104 is varied to accommodate varying foot sizes. Width of the support band 102, 104 also is varied to accommodate varying foot sizes. Additionally, the length of the support band can be adjustable on the dynamic foot-arch support device 100 to accommodate varying foot sizes. In one embodiment, the support band 102, 104 is an elongated, flexible elastic material. The flexible elastic material can be, for example, elastic in length and inelastic in width, among other combinations, to provide various support methods to the arch and structures of the foot.

The support band 102, 104 includes a loop formed at the upper end 822 through which to place a foot. The loop is positioned around an area about or just below an ankle portion of the foot. By way of example, the upper end 822 is stitched and attached to a lateral side of the support band 102, 104 to form a top loop for placement around or just below the ankle of the wearer. The opening created by the loop provides for proper placement of the support band 102, 104 about the ankle and the medial arch. By way of example, the loop in the support band 102, 104 shown is placed to rest just below the medial and lateral ankle bones. Alternatively, the support band 102, 104 and loop are integrally formed in a single molded piece that does not require stitching, or the like, to create a loop.

The lower end 824 of the support band 102, 104 is configured to wrap from the medial arch area about or just below the medial, or inside, ankle portion of the foot and be rotated to an underside of the foot and cross diagonally across the plantar surface area for secure attachment below the underside of the foot, providing tension to support to an arch area of the foot. For example, the lower end 824 of the support band 102, 104 terminates under the metatarsal phalange distal heads.

As depicted in FIGS. 1-7, the support band 102, 104 with a loop formed in it has a heel bone portion 116, 126, a medial arch portion 114, 124, and a lower portion 118, 128 about both a right foot 110 and a left foot 120. By way of example, the wearer's foot is placed through the loop portion of the support band 102, 104 with the heel bone portion covering the area of the heel bone and the Achilles tendon area. The medial arch portion wraps from the medial ankle portion of the foot to the underside of the foot to traverse diagonally across the plantar surface area. The lower portion 118, 128 is utilized for attachment to footwear, a sock, a stocking, a forefoot cover, or the like, providing tension in the support band to support to an arch area of the foot.

In various embodiments, the dynamic foot-arch support device 100 includes a shoe sole 119, 129 (shown separated from the shoe structure for illustrative purposes only. The shoe sole 119, 129 is an accessory to the support band. The shoe sole 119, 129 is cut in the general shape of 810 as depicted in FIG. 8. A shoe sole 119, 129 is securely attached to the lower portion 118, 128 of the support band 102, 104 and configured for insertion of a foot. Tension is formed on the support band between the shoe sole 119, 129 and the loop placed around an area about or just below an ankle portion of the foot providing support to the plantar surface.

In alternative embodiments, the dynamic foot-arch support device 100 is utilized with other anchor components such as, but not limited to, a shoe, boot, sandal, sock, or stocking. For example, in one embodiment, the lower portion 118, 128 of the support band is placed to rest under the $2^{nd}$ through the $4^{th}$ or $5^{th}$ metatarsal phalange distal heads and securely attached to an inner sole surface of a footwear 200. The tension is formed on the support band between the inside sole area and the loop around an area about or just below an ankle portion of the foot providing support to the plantar surface.

Alternatively, the dynamic foot-arch support device 100, as a whole, is integrally formed with a sock or stocking. A wearer of such a support device 100 simply pulls on the device as a sock or stocking and the arch support structure is already integrated.

Figure 7:
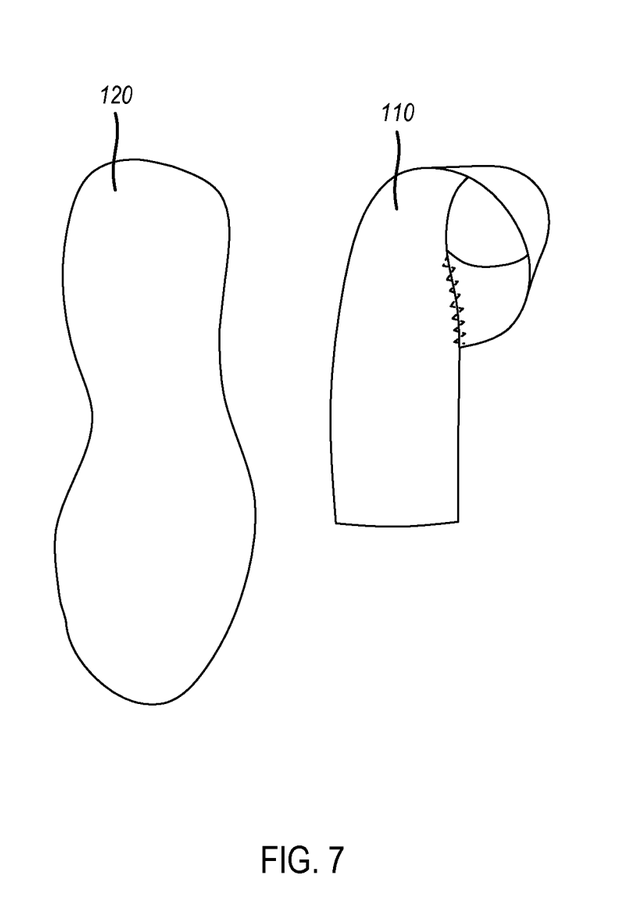
FIG. 7 is a top plan view of the dynamic foot-arch support assembly, illustrating, in particular, the support band and shoe sole, according to an embodiment of the technology.

With reference now to FIG. 7, support band 102, 104 is shown unattached from any anchor device. The support band can be attached to the shoe sole 119, 129 or to another anchor device such as a shoe, or the like. Additionally, the support band 102, 104 can be integrally formed with a sock, stocking, or the like.

Although this technology has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the invention and are intended to be covered by the following claims.

What is claimed is:

1. A dynamic foot-arch support assembly for dynamically supporting an arch and structures of a foot throughout phases of biomechanical movement of the foot during weight-beating activities, the assembly comprising:
    a support band having a generally rectangular shape having a length and a width, comprised of an elongated, flexible material that is elastic in length and inelastic in width, an upper end and a lower end, the support band forming a fixed loop at the upper end through which to place a foot and position the fixed loop around an area about or just below an ankle portion of the foot, the lower end configured to wrap from an inside of the area about or just below the ankle portion of the foot and rotate 180 degrees to an underside of the foot and across a plantar surface area for secure attachment below the underside of the foot, the support band thereby configured to provide an adjustable tension to support to an arch area of the foot; and a footwear having a sole, at least one portion of the support band integrally formed with the sole at a predetermined angle.

2. The dynamic foot-arch support assembly of claim 1, wherein the footwear is a shoe.

3. The dynamic foot-arch support assembly of claim 2, wherein the footwear is a boot.

4. A dynamic foot-arch support assembly for dynamically supporting an arch and structures of a foot throughout phases of biomechanical movement of the foot during weight-bearing activities, the assembly comprising:

a support band having a generally rectangular shape having a length and a width, comprised of an elongated, flexible material that is elastic in length and inelastic in width, an upper end and a lower end, the support band forming a fixed loop at the upper end through which to place a foot and position the fixed loop around an area about or just below an ankle portion of the foot, the lower end configured to wrap from an inside of the area about or just below the ankle portion of the foot and rotate 180 degrees to an underside of the foot and across a plantar surface area for secure attachment below the underside of the foot, the support band thereby configured to provide an adjustable tension to support to an arch area of the foot; and a footwear having a sole, the lower end of the support band secured to the sole at a predetermined angle.

5. The dynamic foot-arch support assembly of claim 4, wherein the footwear is a shoe.

6. The dynamic foot-arch support assembly of claim 4, wherein the footwear is a boot.

7. A dynamic foot-arch support assembly for dynamically supporting an arch and structures of a foot throughout phases of biomechanical movement of the foot during weight-bearing activities, the assembly comprising:

a support band having a generally rectangular shape having a length and a width, comprised of an elongated, flexible material that is elastic in length and inelastic in width, an upper end and a lower end, the support band forming a fixed loop at the upper end through which to place a foot and position the fixed loop around an area about or just below an ankle portion of the foot, the lower end configured to wrap from an inside of the area about or just below the ankle portion of the foot and rotate 180 degrees to an underside of the foot and across a plantar surface area for secure attachment below the underside of the foot, the support band thereby configured to provide an adjustable tension to support to an arch area of the foot; and a footwear having a sole, the lower end of the support band releasably attached to the sole at a predetermined angle.

8. The dynamic foot-arch support assembly of claim 7, wherein the footwear is a shoe.

9. The dynamic foot-arch support assembly of claim 7, wherein the footwear is a boot.

\* \* \* \* \*